United States Patent
Tsutsui et al.

(10) Patent No.: US 7,742,162 B2
(45) Date of Patent: Jun. 22, 2010

(54) MASK DEFECT INSPECTION DATA GENERATING METHOD, MASK DEFECT INSPECTION METHOD AND MASK PRODUCTION METHOD

(75) Inventors: Tomohiro Tsutsui, Tokyo (JP); Ryoji Yoshikawa, Yokohama (JP); Osamu Ikenaga, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 135 days.

(21) Appl. No.: 12/187,868

(22) Filed: Aug. 7, 2008

(65) Prior Publication Data

US 2009/0046280 A1 Feb. 19, 2009

(30) Foreign Application Priority Data

Aug. 8, 2007 (JP) ............................. 2007-206953

(51) Int. Cl.
*G01N 21/00* (2006.01)
(52) U.S. Cl. .............. 356/237.4; 356/239.1; 356/239.3; 356/237.2
(58) Field of Classification Search ... 356/237.1–241.6, 356/426–431, 600–640
See application file for complete search history.

(56) References Cited

U.S. PATENT DOCUMENTS

| 4,532,650 | A | * | 7/1985 | Wihl et al. | .................. 382/144 |
| 4,930,889 | A | * | 6/1990 | Van Donselaar et al. | . 356/237.6 |
| 7,289,201 | B2 | * | 10/2007 | Matsumoto, Junichi | .. 356/239.1 |
| 2006/0280358 | A1 | * | 12/2006 | Ishikawa | ..................... 382/149 |
| 2006/0292458 | A1 | | 12/2006 | Tsutsui et al. | |

* cited by examiner

*Primary Examiner*—Gregory J Toatley, Jr.
*Assistant Examiner*—Jarreas C Underwood
(74) *Attorney, Agent, or Firm*—Finnegan, Henderson, Farabow, Garrett & Dunner, L.L.P.

(57) ABSTRACT

According to a mask defect inspection data generating method, a distance between inspection areas neighboring in a predetermined direction is calculated based on inspection area control information defined in photomask inspection data. It is determined whether or not the calculated distance between inspection areas is less than a predetermined distance. When it is determined that the distance between inspection areas is less than a predetermined distance, the inspection area is combined to produce an optimization inspection area. The produced optimization inspection area information is defined in inspection layout data for making a reference in die-to-database defect inspection.

14 Claims, 6 Drawing Sheets

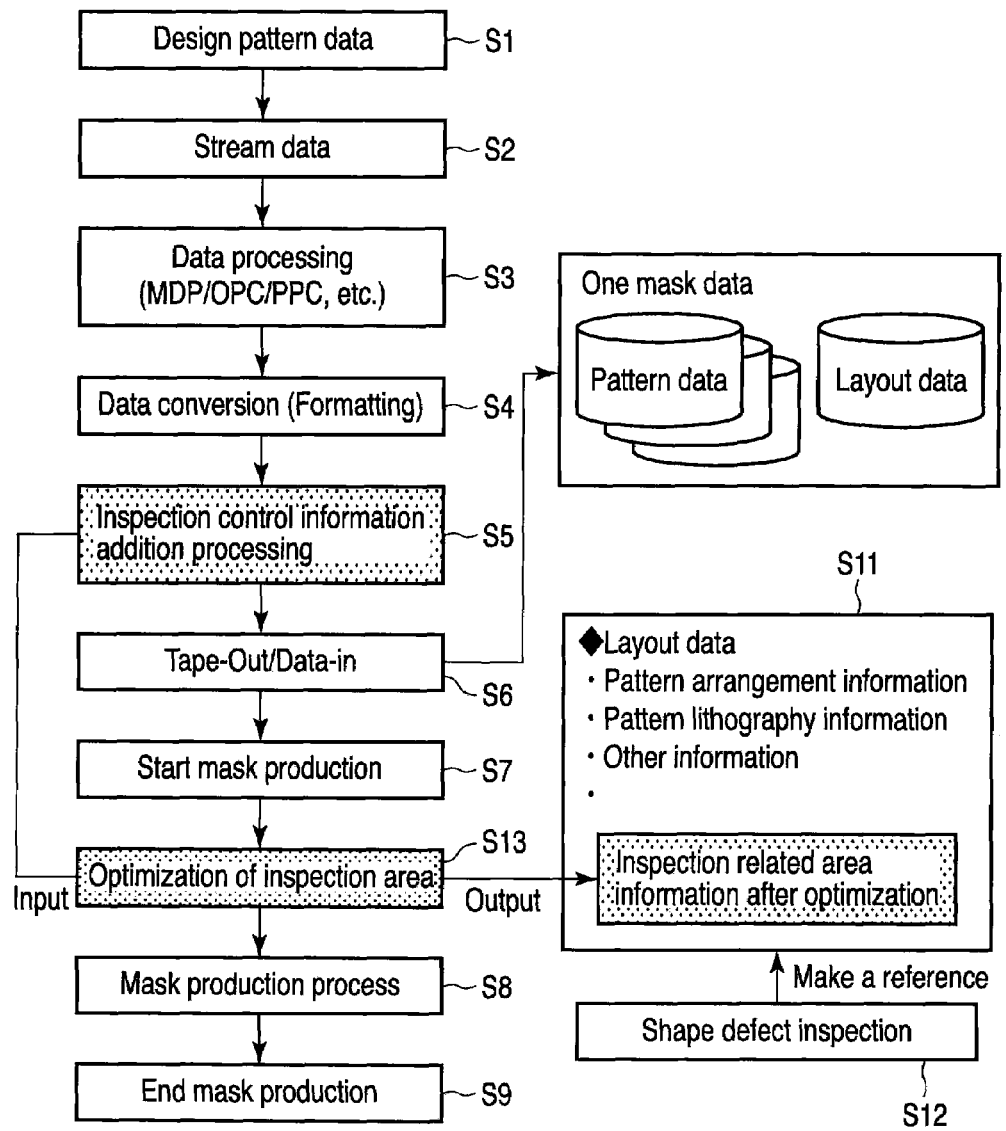
F I G. 1

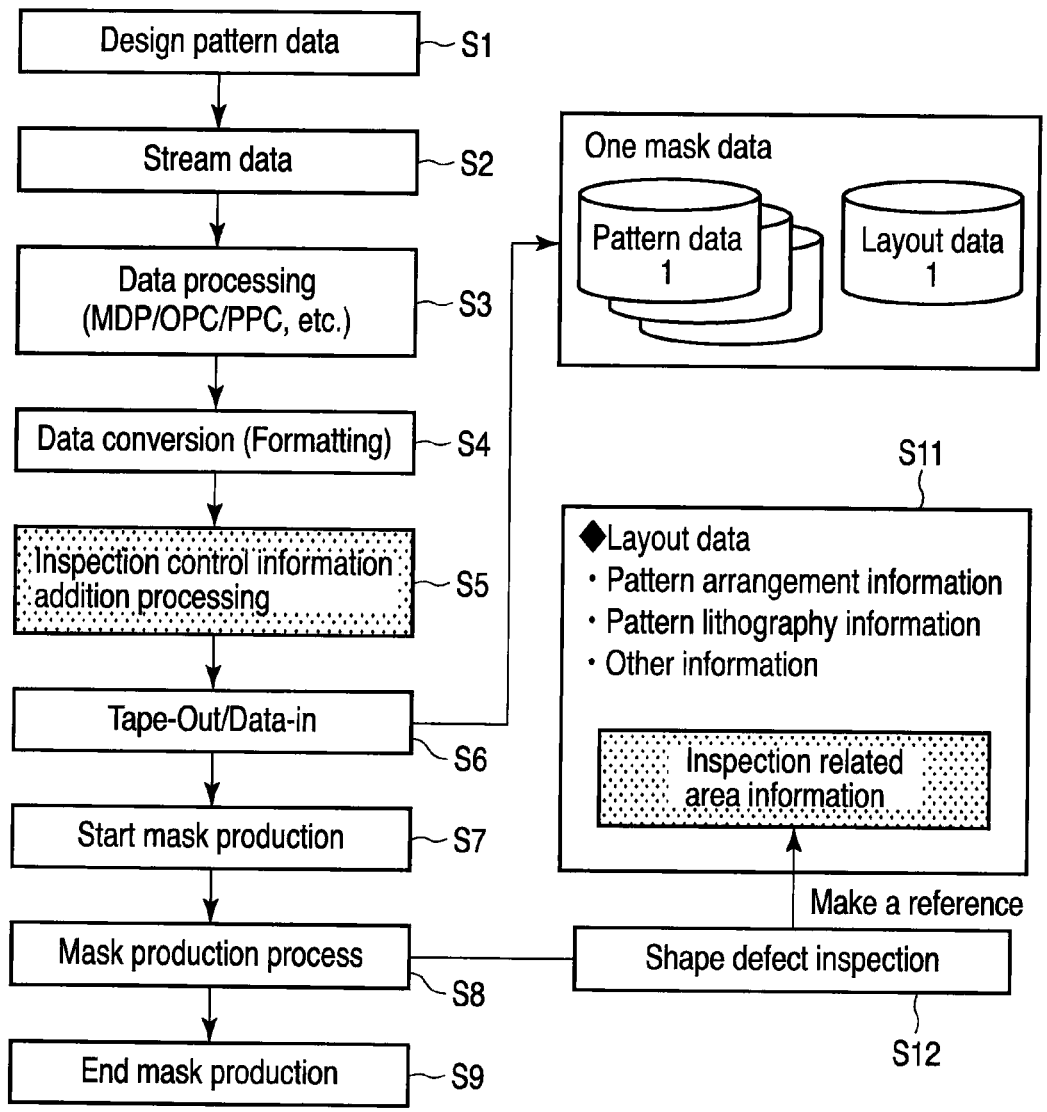
F I G. 6

MASK DEFECT INSPECTION DATA GENERATING METHOD, MASK DEFECT INSPECTION METHOD AND MASK PRODUCTION METHOD

CROSS-REFERENCE TO RELATED APPLICATIONS

This application is based upon and claims the benefit of priority from prior Japanese Patent Application No. 2007-206953, filed Aug. 8, 2007, the entire contents of which are incorporated herein by reference.

BACKGROUND OF THE INVENTION

1. Field of the Invention

The present invention relates to a technique of producing a photomask used for manufacturing a semiconductor device. In particular, the present invention relates to a mask defect inspection data generating method for generating inspection data used for a shape defect inspection process, and to a mask defect inspection method using inspection data obtained by the foregoing method.

In addition, the present invention relates to a mask production method including a process of inspecting defect using a mask defect inspection method.

2. Description of the Related Art

A photomask used for manufacturing a semiconductor device has the following problem. Specifically, with advance in pattern scale reduction, it is difficult to detect a microdefect formed on a mask. In order to detect the microdefect, inspection is required using high inspection sensitivity. For this reason, the inspection time becomes longer compared with the conventional case, and thus, inspection throughput decreases. In addition, a pattern forming region becomes wider compared with the conventional case; for this reason, an increase of inspection time by inspection area enlargement is also one of the problem.

The photomask defect inspection has the following two cases. One is the case of inspecting the entire surface of a pattern forming region. Another is the case of inspecting a specified area in the pattern forming region. The latter case is called an area limited inspection. In the actual mask defect inspection, the foregoing inspection method is employed. Besides, the following inspection method is employed. According to the inspection method, an area having defects allowable in the inspected area is previously defined as an inspection excluded area. If a defect detected in inspecting the entire surface of the pattern forming region or an area limited inspection area exists within the inspection excluded area, the defect is not counted as a defect.

The present defect inspection is made in combination with the foregoing methods. For example, according to die to database, when the area limited inspection and the area excluded inspection are made, coordinate information of a previously inspected area and an area excluding inspection is defined in inspection layout data. An inspection apparatus makes a defect inspection according to the area information defined in the data to determine whether or not a defect exists on a mask. The foregoing die to database detects a defect in the following manner. Specifically, a comparison is made between the following two data images, and thereby, the different portion between two data images is defined as a defect. One is a data image (sensor data) generated by capturing a pattern image formed on a photomask using a CCD camera of the inspection apparatus. Another is a data image (reference data) generated from design data.

The foregoing inspection methods have the following advantages. Namely, the specified area only is inspected, and partial areas in the inspection area are given as an inspection excluded area. However, the inspection apparatus makes an inspection according to the following operation. Specifically, the inspection apparatus continuously moves a designated area with an inherent stripe width of the apparatus in the X direction while repeating step movement in the Y direction. For this reason, a stripe turn is generated at the inspection area end in the X direction. The foregoing turn is a factor of temporarily stopping continuous movement. Therefore, the turn becomes much by setting an inspection excluded area, and thereby, the inspection time becomes long by the increased turn. As a result, the inspection time becomes remarkably long depending on an area setting method, and this is a problem of reducing throughput.

BRIEF SUMMARY OF THE INVENTION

According to one aspect of the present invention, there is provided a mask defect inspection data generating method comprising:

extracting inspection area control information showing a plurality of inspection areas except an inspection excluded area having no need of inspection from a pattern inspection region based on photomask inspection data;

calculating a distance between inspection areas neighboring in a predetermined direction based on the extracted inspection area control information;

determining whether or not the calculated distance between inspection areas is less than a predetermined distance;

combining the inspection areas to produce an optimization inspection area when it is determined that the calculated distance between inspection areas is less than a predetermined distance, and producing the inspection areas as an optimization inspection area when it is not determined that the distance is less than the predetermined distance; and defining the produced optimization inspection area information in inspection layout data for making a reference in a die-to-database defect inspection.

According to another aspect of the present invention, there is provided a mask defect inspection method comprising:

extracting inspection area control information showing a plurality of inspection areas except an inspection excluded area having no need of inspection from a pattern inspection region based on photomask inspection data;

calculating a distance between inspection areas neighboring in a predetermined direction based on the extracted inspection area control information;

determining whether or not the calculated distance between inspection areas is less than a predetermined distance;

combining the inspection areas to produce an optimization inspection area when it is determined that the calculated distance between inspection areas is less than a predetermined distance, and producing the inspection areas as an optimization inspection area when it is not determined that the distance is less than the predetermined distance;

defining the produced optimization inspection area information in inspection layout data for making a reference in a die-to-database defect inspection;

detecting a pattern formed on the photomask every optimization inspection area using an inspection optical system based on the inspection layout data to acquire sensor data; and comparing the sensor data with the corresponding reference data to determine whether or not a defect exists.

According to another aspect of the present invention, there is provided a mask production method of forming a shield film or half-tone film pattern on a transparent substrate based on photomask design data, comprising:

extracting inspection area control information showing a plurality of inspection areas except an inspection excluded area having no need of inspection from a pattern inspection region based on photomask inspection data;

calculating a distance between inspection areas neighboring in a predetermined direction based on the extracted inspection area control information;

determining whether or not the calculated distance between inspection areas is less than a predetermined distance;

combining the inspection areas to produce an optimization inspection area when it is determined that the calculated distance between inspection areas is less than a predetermined distance, and producing the inspection areas as an optimization inspection area when it is not determined that the distance is less than the predetermined distance;

defining the produced optimization inspection area information in inspection layout data for making a reference in a die-to-database defect inspection;

detecting a pattern formed on the photomask every optimization inspection area using an inspection optical system based on the inspection layout data to acquire sensor data; and comparing the sensor data with the corresponding reference data to determine whether or not a defect exists.

BRIEF DESCRIPTION OF THE SEVERAL VIEWS OF THE DRAWING

FIG. 1 is a flowchart to explain a photomask inspection data generating method according to one embodiment of the present invention;

FIG. 6 is a flowchart to explain a normal inspection data generating flow;

Figure 2:
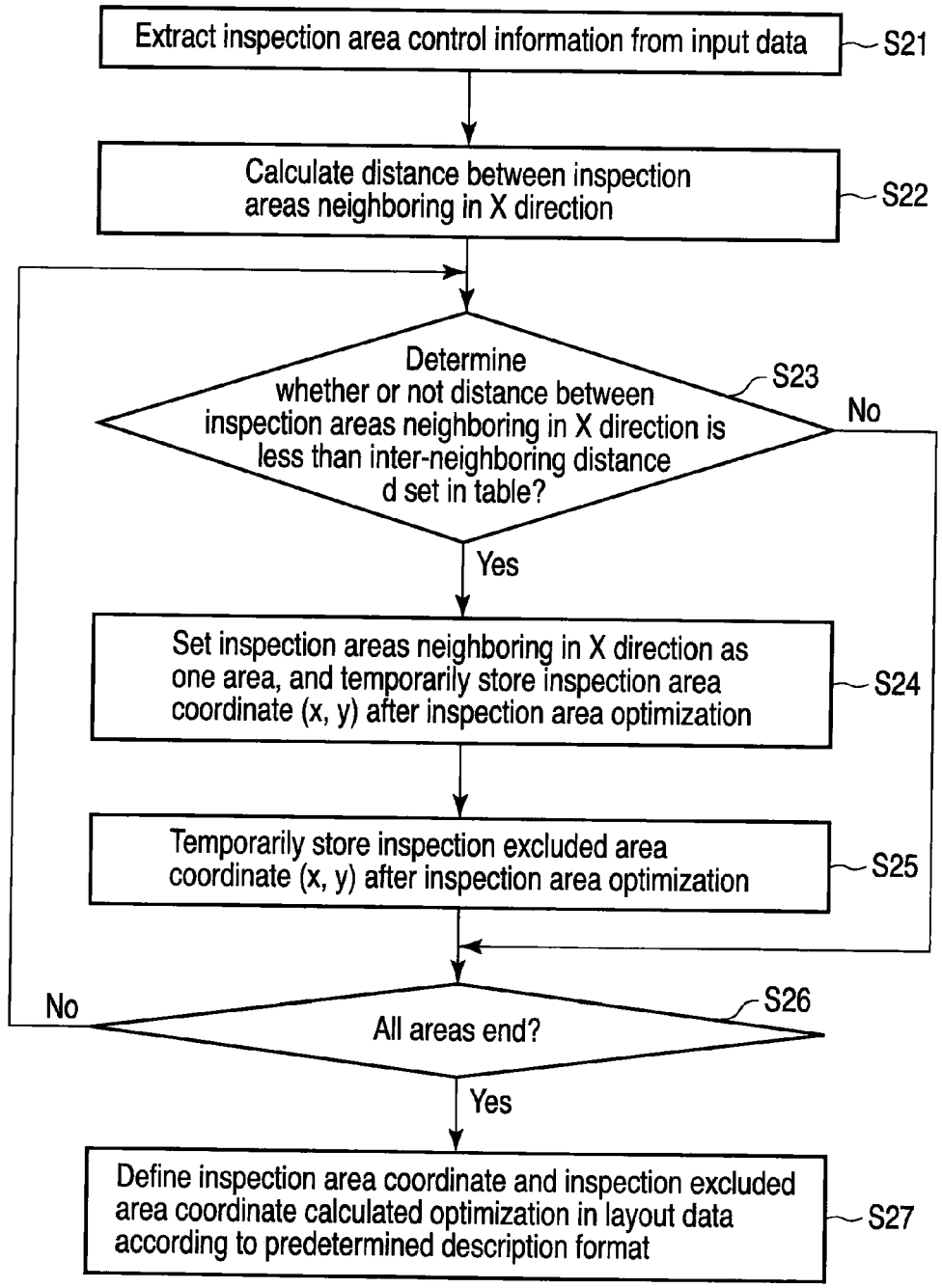
FIG. 2 is a flowchart to explain an inspection area optimization in this embodiment.

DETAILED DESCRIPTION OF THE INVENTION (Principle of the Invention)

The basic principle of the present invention will be hereinafter described before an explanation of embodiments.

FIG. 6 is a view to explain a normal inspection data generating flow given as a reference example of the present invention. A desired pattern for manufacturing a semiconductor device is designed using various CAD tools to generate design data (S1). The design data is output according to a stream format such as GDSII and OASIS (S2).

Then, the following various processings are performed with respect to the design data (stream data). One is mask data processing (MDP), and another is optical proximity correction (OPC). Another is process proximity correction (PPC). Another is an interlayer data operation (e.g., AND, OR and XOR operations between graphics) for generating pattern data to be formed in a photomask from the design data. In this case, according to the foregoing MDP, a mask pattern is changed using a graphic operation and a design rule checker (DRC). The foregoing OPC is a processing for correcting optical proximity effect when a pattern is transferred from the photomask to a wafer using an exposure device. The foregoing PPC is a processing for correcting wafer pattern deformation by process proximity effect caused when the exposed pattern is patterned via development and etching.

If necessary, CAD processing is carried out in combination with dimensional correction and tone reversal. Thereafter, formatting (data conversion) to an inspection data format capable of inputting to a defect inspection apparatus is executed (S4).

Then, inspection control information addition processing is carried out (S5). In this way, when a specified area only in a pattern forming region is inspected, inspection area coordinate information is defined in layout data. In addition, even if a defect exists in an inspection target area, when the defect does not count as a defect, inspection excluded coordinate information showing an area excluding the inspection (no count even if a defect exists) is defined in the layout data (S11). In this case, the inspection area information defined in the layout data of the inspection data simply describes an inspection area. Thus, the inspection time is not quite considered.

Data obtained in the foregoing procedures S1 to S5 is taped out, and then, input to a mask production apparatus (S6). Thereafter, a mask is produced using an exposure device, developer and etching device (S7 to S9). Specifically, an LSI pattern is exposed on a resist using an exposure device with respect to mask blanks formed with a shield film or half-tone film on a transparent substrate. Then, the resist is developed using a developer to form a resist pattern. Thereafter, the shield film or the half-tone film is selectively etched by an etching device using the resist pattern as a mask, and thus, a photomask is produced. In a mask production process, a shape inspection is made using a defect inspection apparatus in order to make a comparison between a pattern actually formed on the mask with the design pattern (S12).

In a shape inspection process, the defect inspection apparatus refers to inspection data to generate reference data for making a comparison with a pattern image formed on the mask. The defect inspection apparatus makes a comparison between data obtained from the pattern image formed on the mask and the reference data to determine the existence of a defect on the mask.

Figure 7:
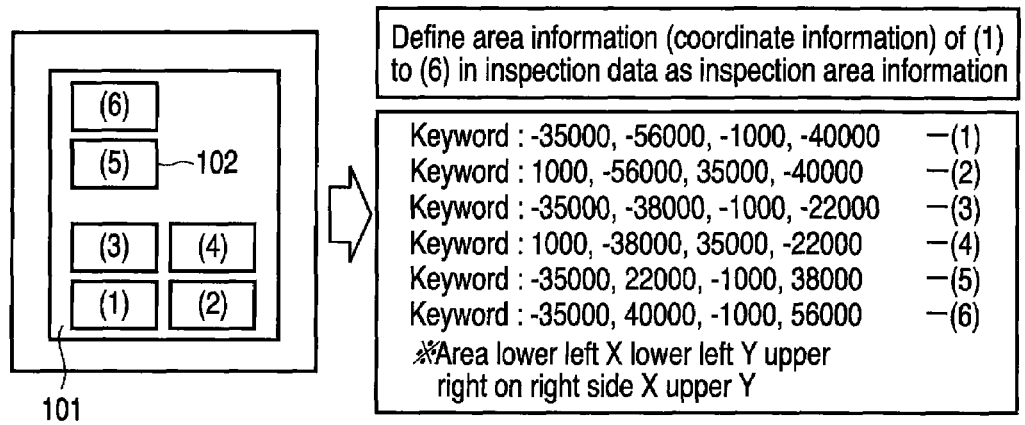
FIG. 7 is a top plan view showing an inspection area designation example according to the flow of FIG. 6.

FIG. 7 shows a method of designating the foregoing area limited inspection area. As shown in FIG. 7, when inspection areas 102 ((1) to (6)) only in a pattern forming region 101 are inspected, each area information of (1) to (6) is defined in the inspection layout data according to the inspection control information addition processing (S5) of the flow shown in FIG. 6. The description of the area information is a format readable by the defect inspection apparatus.

Figure 8:
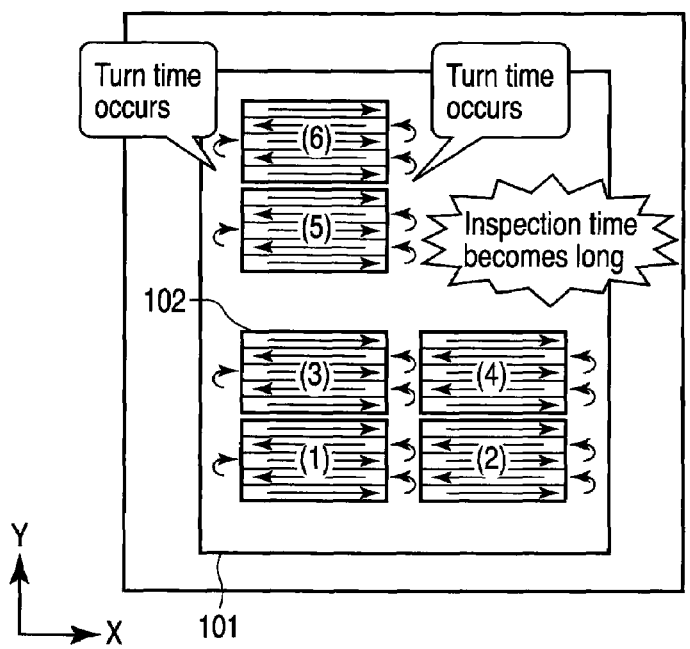
FIG. 8 is a top plan view showing a problem of the inspection area designation example according to the flow of FIG. 6.

FIG. 8 shows a problem in the foregoing area limited inspection designation. The inspection apparatus makes an inspection in the following manner. Specifically, the inspection area is inspected via continuous movement with an inherent stripe width in the X direction and step movement in the Y direction. For this reason, a turn occurs at the area end in the X direction; as a result, time is taken to turn in addition to the actual inspection time. If a longitudinal inspection area is large, the inspection time becomes long.

In order to solve the foregoing problem, according to one embodiment of the present invention, the turn time is reduced, and thereby, the total inspection time is shortened. One embodiment of the present invention will be described below.

EMBODIMENT

FIG. 1 is a view to explain the flow of a photomask inspection data generating method according to one embodiment of the present invention.

S1 to S9 of the flow is basically the same as FIG. 6. According to this embodiment, inspection area setting is optimized (S13) before mask inspection (S12) after data input (S6). According to this embodiment, inspection data generated by the foregoing optimization is given as optimization inspection area data, and then, a defect inspection is made using the foregoing data.

FIG. 2 is a flowchart to explain an inspection area optimization flow according to this embodiment.

Inspection area information is extracted from input inspection layout data (S21). Specifically, various processings and conversion are performed with respect to photomask design data, and then, data thus prepared is input. Inspection area control information showing a plurality of inspection areas except inspection excluded areas having no need of inspection is extracted from a pattern forming region.

A distance between scan areas neighboring in the X direction is calculated (S22). In this case, if the neighboring area is plural, all distances between scan areas are calculated.

A comparison is made between the distance calculated in S22 with information (inter-neighboring distance d) stored in an optimization identify table previously defined based on the inspection apparatus performance (S23).

If the inter-neighboring distance d is too long, scan time of non-inspection areas becomes long. Thus, there is the case where advantage is obtained by making an inspection in a state that the area is divided. In other words, the following cases should be considered depending on the relationship between scan time of non-inspection area and turn time. One is the case where it is best to inspect the area in a state of being divided. Another is the case where it is best to merge the area.

If turn time<scan time of non-inspection area, the area is inspected in a state of being divided If turn time>scan time of non-inspection area, the area is merged.

Thus, the inter-neighboring distance d is set to a distance satisfying the following condition. According to the foregoing condition, the sum of the total turn time in the inspection area is larger than the total scan time of non-inspection areas.

If the distance between inspection areas is less than a registration distance d stored in the optimization identify table, areas neighboring in the X direction is defined as one area. Then, the lower left coordinate (x, y) and the lower right coordinate (x, y) of the area are temporarily stored on a disk as an optimization inspection area after optimization (S24). In this case, a non-inspection area between areas neighboring in the X direction before optimization is set as a non-inspection area after optimization (S25). Then, the lower left coordinate (x, y) and the lower right coordinate (x, y) of the non-inspection area are temporarily stored on a disk. If three or more inspection areas are neighboring, the same procedure is repeated.

Figure 3:
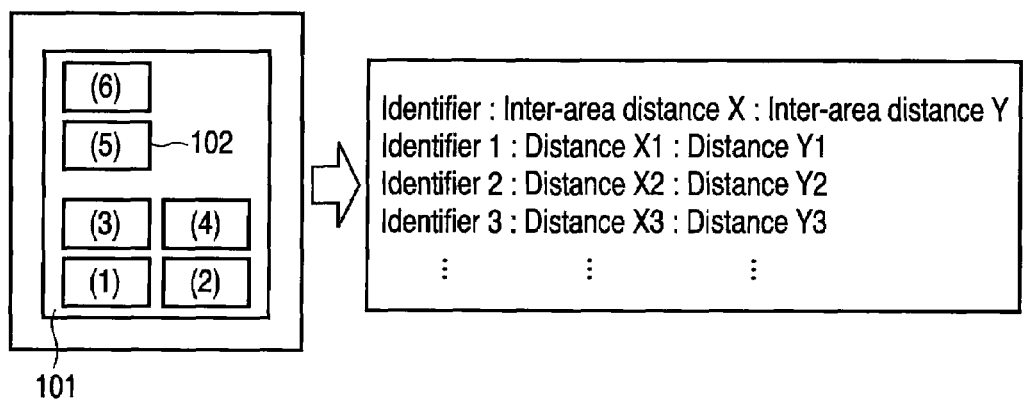
FIG. 3 is an aptness identifying table referred for determining whether or not an inspection area is optimized in this embodiment.

The registration information stored in the optimization identify table is classified using keywords such as mask grade, product and generation. For example, as seen from FIG. 3, the information is previously registered according to combination of the keyword and an inter-area distance. The inter-area distance registered in the optimization identify table is determined depending on specific features of the inspection apparatus. For example, an inspection pixel is different every mask grade, and a stage speed is different every inspection pixel. Therefore, there is a possibility that the inter-area distance is changed depending on the condition of the apparatus. The inter-area distance is a value given as the following judgment reference. Namely, the value is used for judge which time when a stage moves the inspection excluded area held between inspection areas or turn time at stripe end is shorter in the total inspection time. The identify information format is not limited to the description of the embodiment; in this case, other format may be used.

It is determined as to whether or not optimization ends with respect to all inspection areas (S26). If the optimization does not end, the procedure returns to S23, and then, inspection area optimization is performed with respect to another inspection area.

If the optimization ends, the finally calculated inspection area and the inspection excluded area are defined in inspection layout data as an optimization inspection area after optimization and an optimization inspection excluded area (S27). In this case, the inspection area information before optimization defined in the original inspection layout data is erased. If the inspection excluded area information exists in the original data, optimization inspection excluded area information newly added to the inspection excluded area by optimization is additionally described in the inspection excluded area of the original data.

A defect inspection is made using the foregoing optimization inspection data to inspect the existence of defect on a mask.

Figure 4:
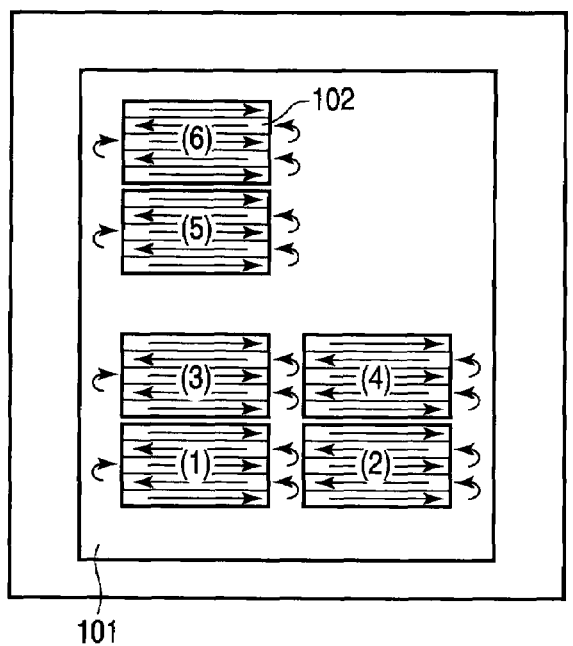
FIG. 4 is a top plan view showing area designation before inspection area optimization.

FIG. 4 shows one example of area limited inspection designation before optimization. According to the designation, areas (1) to (6) are defined in inspection layout data as area limited inspection information.

Figure 5:
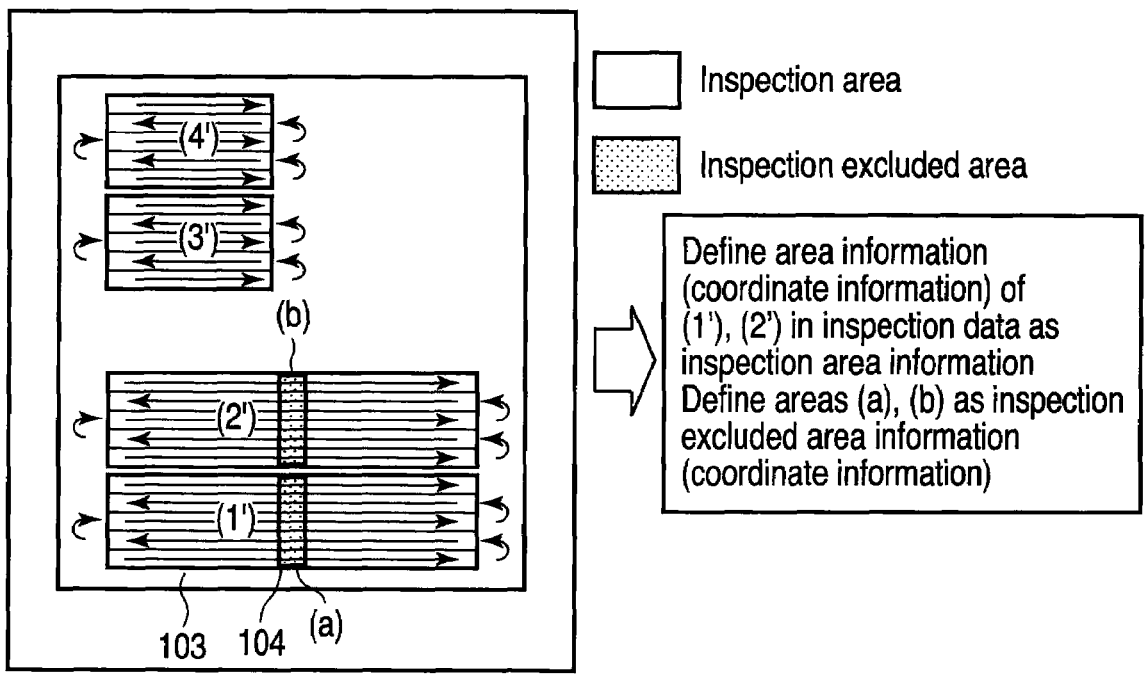
FIG. 5 is a top plan view showing area designation after inspection area optimization.

FIG. 5 shows area limited inspection designation after layout optimization. Areas (5) and (6) of FIG. 4 has no area neighboring in the X direction; for this reason, areas (3') and (4') the same as the area before optimization are given as the inspection area after optimization. In areas (1)-(2) and areas (3)-(4), two inspection areas are neighboring in the X direction, and the inter-neighboring distance is less than the distance registered in the table of FIG. 3. Therefore, these areas (1)-(2) and (3)-(4) are set as (1') and (2'), respectively. In this case, the lower left coordinate (x, y) and the upper right coordinate (x, y) of the areas (1') and (2') are temporarily stored on a disk as an optimization inspection area 103 after optimization. Areas (a) and (b) of the areas (1') and (2') are inspection excluded area. Therefore, each coordinate of these areas (a) and (b) is temporarily stored on a disk as an optimization inspection excluded area.

Optimization inspection area information after optimization is defined in inspection layout data, and the inspection excluded area after optimization is defined as an optimization inspection excluded area. If the inspection excluded area exists in the original data, an area newly added to the inspection excluded area by optimization is additionally described as an inspection excluded area of the original data. Inspection is made using these inspection data, and thereby, determining whether or not a defect exists on a photomask.

In the actual inspection, a shape inspection is carried out using a defect inspection apparatus in the mask production process of S8 to compare the actually formed pattern on the mask with the design pattern (S12).

The defect inspection apparatus captures a pattern image formed on a photomask using a CCD camera of the inspection apparatus to generate a data image (sensor data). In this case, a stage on which a mask is placed continuously moves in the X direction while makes step movement in the Y direction.

In the shape inspection process, the defect inspection apparatus refers to the inspection data to generate reference data for making a comparison with the pattern image formed on the mask. In this way, the defect inspection apparatus compares data obtained from the pattern image formed on the mask with the reference data to determine whether or not a defect exists on the mask.

In this case, the inspection area is optimized; therefore, the number of stripe turn times in the inspection is reduced. Thus, this serves to shorten the inspection time.

According to this embodiment, the defect inspection area is optimized, and thereby, it is possible to shorten the inspection time for detecting a defect on the photomask in die to database defect inspection. Thus, this serves to reduce time taken to manufacture a mask and the mask manufacturing cost.

The following various inspection related information is previously defined in the inspection data used for the die to database shape defect inspection. One is information for inspecting specified area only in the pattern forming region by a mask designer. Another is information such that a defect is not counted even if the defect exists in the inspection area. Of the defined inspection related information, information showing the inspection area is fetched, and the existence of a plurality of neighboring areas and the distance are calculated. Then, the calculated distance between inspection areas is compared with a value previously defined based on the inspection apparatus performance to determine whether or not the calculated distance is less than a predetermined distance. Based on the determination result, the optimization inspection area is calculated, and the calculated optimization inspection area information is defined in the inspection data. In this way, a defect inspection is made using the optimization inspection data. Therefore, it is possible to reduce stripe turn at the inspection area end, which is a factor of increasing the inspection time in the conventional inspection area designation method; as a result, the inspection time can be shortened.

MODIFICATION EXAMPLE

The present invention is not limited to the foregoing embodiment. According to this embodiment, a photomask is used as an exposure mask. The present invention is not necessarily limited to the photomask, and applicable to an EUV mask. In addition, the present invention is not limited to mask defect inspection data generation or mask defect inspection. The present invention is applicable to a method of producing a mask using the foregoing data and inspection. The present invention is further applicable to a method of manufacturing a semiconductor device using the mask.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A mask defect inspection data generating method comprising:
    extracting inspection area control information showing a plurality of inspection areas except an inspection excluded area having no need of inspection from a pattern inspection region based on photomask inspection data;
    calculating a distance between inspection areas neighboring in a predetermined direction based on the extracted inspection area control information;
    determining whether or not the calculated distance between inspection areas is less than a predetermined distance;
    combining the inspection areas to produce an optimization inspection area when it is determined that the calculated distance between inspection areas is less than a predetermined distance, and producing the inspection areas as an optimization inspection area when it is not determined that the distance is less than the predetermined distance; and
    defining the produced optimization inspection area information in inspection layout data for making a reference in a die-to-database defect inspection.

2. The method according to claim 1, wherein in order to calculate a distance between neighboring inspection areas in the predetermined direction, when a direction of continuously moving the photomask with respect to an inspection optical system is set X and a direction of step movement is set as Y, a distance between neighboring inspection areas in the X direction is calculated.

3. The method according to claim 1, wherein when the inspection area is combined to produce an optimization inspection area, an inspected area between inspection areas before combination is defined as an inspection excluded area.

4. The method according to claim 3, wherein the predetermined distance is set to a distance such that the sum of the total scan time in the inspection excluded area when the inspection area is combined to produce an optimization inspection area is equal to the sum of turn time between the inspection areas before combination.

5. The method according to claim 1, wherein the predetermined distance is previously defined based on an inspection apparatus performance, and stored in an optimization identify table.

6. The method according to claim 5, wherein registration information stored in the optimization identify table is classified every keyword such as mask grade, product and generation.

7. A mask defect inspection method comprising:
    extracting inspection area control information showing a plurality of inspection areas except an inspection excluded area having no need of inspection from a pattern inspection region based on photomask inspection data;
    calculating a distance between inspection areas neighboring in a predetermined direction based on the extracted inspection area control information;
    determining whether or not the calculated distance between inspection areas is less than a predetermined distance;
    combining the inspection areas to produce an optimization inspection area when it is determined that the calculated distance between inspection areas is less than a predetermined distance, and producing the inspection areas as an optimization inspection area when it is not determined that the distance is less than the predetermined distance;
    defining the produced optimization inspection area information in inspection layout data for making a reference in a die-to-database defect inspection;
    detecting a pattern formed on the photomask every optimization inspection area using an inspection optical system based on the inspection layout data to acquire sensor data; and comparing the sensor data with the corresponding reference data to determine whether or not a defect exists.

8. The method according to claim 7, wherein in order to calculate a distance between neighboring inspection areas in the predetermined direction, when a direction of continuously moving the photomask with respect to an inspection optical system is set X and a direction of step movement is set as Y, a distance between neighboring inspection areas in the X direction is calculated.

9. The method according to claim 7, wherein when the inspection area is combined to produce an optimization inspection area, an inspected area between inspection areas before combination is defined as an inspection excluded area.

10. The method according to claim 9, wherein the predetermined distance is set to a distance such that the sum of the total scan time in the inspection excluded area when the inspection area is combined to produce an optimization inspection area is equal to the sum of turn time between the inspection areas before combination.

11. The method according to claim 7, wherein in order to acquire the sensor data, the mask is continuously moved in a X direction with respect to the inspection optical system while is step-moved in a Y direction, and in order to calculate a distance between neighboring inspection areas in the predetermined direction, a distance between neighboring inspection areas in the X direction is calculated.

12. The method according to claim 7, wherein the predetermined distance is previously defined based on an inspection apparatus performance, and stored in an optimization identify table.

13. The method according to claim 12, wherein registration information stored in the optimization identify table is classified every keyword such as mask grade, product and generation.

14. A mask production method of forming a shield film or half-tone film pattern on a transparent substrate based on photomask design data, comprising:

extracting inspection area control information showing a plurality of inspection areas except an inspection excluded area having no need of inspection from a pattern inspection region based on photomask inspection data;

calculating a distance between inspection areas neighboring in a predetermined direction based on the extracted inspection area control information;

determining whether or not the calculated distance between inspection areas is less than a predetermined distance;

combining the inspection areas to produce an optimization inspection area when it is determined that the calculated distance between inspection areas is less than a predetermined distance, and producing the inspection areas as an optimization inspection area when it is not determined that the distance is less than the predetermined distance;

defining the produced optimization inspection area information in inspection layout data for making a reference in a die-to-database defect inspection;

detecting a pattern formed on the photomask every optimization inspection area using an inspection optical system based on the inspection layout data to acquire sensor data; and comparing the sensor data with the corresponding reference data to determine whether or not a defect exists.

* * * * *